United States Patent [19]
Ghelli et al.

[11] Patent Number: 5,340,364
[45] Date of Patent: Aug. 23, 1994

[54] DEVICE FOR SELECTIVELY DRAWING SAMPLES OF BLOOD FROM TWO SECTIONS OF A LINE AND FOR INJECTING BLOOD INTO SAID LINE

[75] Inventors: Nicola Ghelli, San Pietro in Casale; Ivo Panzani, Mirandola, both of Italy

[73] Assignee: Dideco S.r.l., Mirandola, Italy

[21] Appl. No.: 136,499

[22] Filed: Oct. 14, 1993

Related U.S. Application Data

[63] Continuation of Ser. No. 819,437, Jan. 10, 1992, abandoned.

Foreign Application Priority Data

Jan. 14, 1991 [IT] Italy ............... MI 91A-00067

[51] Int. Cl.[5] .............................................. A61M 1/00
[52] U.S. Cl. ...................................... 604/32; 604/30; 604/4
[58] Field of Search ............... 604/4, 8, 9, 19, 27, 604/30, 32; 73/863.73, 863.82, 863.85, 863.86

[56] References Cited

U.S. PATENT DOCUMENTS

| | | | |
|---|---|---|---|
| 1,853,202 | 4/1932 | Catlin | 604/32 |
| 2,864,254 | 12/1958 | McDonald et al. | |
| 3,048,192 | 8/1962 | Murphy, Jr. | 604/32 X |
| 3,078,848 | 2/1963 | Milbert | 604/32 |
| 3,157,201 | 11/1964 | Littman | 604/32 X |
| 3,780,736 | 12/1973 | Chen | 604/32 |
| 3,834,372 | 9/1974 | Turney | |
| 3,884,082 | 5/1975 | Merciadis | |
| 4,133,736 | 1/1979 | Nakagawa et al. | 73/863.85 X |
| 4,566,480 | 1/1986 | Parham | 604/32 X |
| 4,736,636 | 4/1988 | Fini et al. | 73/863.85 X |
| 5,074,334 | 12/1991 | Onodera | 604/32 X |

*Primary Examiner*—Robert A. Hafer
*Assistant Examiner*—Sam Rimell
*Attorney, Agent, or Firm*—Thomas E. Popovich; David B. Edgeworth

[57] ABSTRACT

The device for selectively drawing samples of blood from two sections of a line and for injecting drugs into the blood comprises a three-way selection element which operates in a seat provided with three connections; the ways are suitable for selectively connecting two of the connections upon manual actuation on the part of an operator. A connection is suitable for receiving a line connected to an arterial blood drawing section; another connection is connected, by means of a duct, to the base of a trap which is open at the top and is suitable for receiving a line connected to a venous blood drawing section; and the third connection comprises a one-way valve allowing flow away from the connection and is connected by means of a duct to the base of a trap which is open at the top and is shaped so as to allow the insertion of a syringe for drawing samples of blood.

7 Claims, 4 Drawing Sheets

DEVICE FOR SELECTIVELY DRAWING SAMPLES OF BLOOD FROM TWO SECTIONS OF A LINE AND FOR INJECTING BLOOD INTO SAID LINE

This is a continuation of U.S. patent application Ser. No. 07/819,437 filed Jan. 10, 1992, now abandoned.

FIELD OF THE INVENTION

The invention relates to a device for selectively drawing samples of blood from two sections of a line and for injecting drugs into the blood.

BACKGROUND OF THE DISCLOSURE

It is known that performing many surgery operations entails the presence of an extracorporeal blood circuit in which various devices, and typically an oxygenation apparatus, are inserted.

During the operation, the conditions of the blood at the inlet and outlet of these devices, i.e. of the blood which operators usually call venous and arterial blood respectively, are checked; for this purpose, devices which allow to separately draw venous and arterial blood, according to the requirements, are commercially available. These devices furthermore, allow performance of another action which is often necessary during said operation, i.e. the injection of drugs into the blood.

Many known devices essentially comprise a coupling for a syringe intended to draw samples of blood and another coupling for a syringe intended to inject drugs, such couplings may be connected by three-way cocks arranged in series; although they are widespread, these devices are not devoid from some disadvantageous drawbacks.

First of all, a certain difficulty in operating with a plurality of three-way cocks is determined by observation of the required functional conditions in these devices, and the possibility of actuation errors. Escape of blood therefrom is a particular difficulty.

A device for selectively sampling from two sections of a line comprising a selection element with a cavity for use with a syringe is described in U.S. Pat. No. 4,736,636.

SUMMARY OF THE DISCLOSURE

The aim of the present invention is to provide a device for selectively drawing samples of blood from two sections of a line and for injecting drugs into said blood, wherein the presetting for providing the required functional conditions is obtained by acting on a single element with a single action and escape of blood is prevented.

The device for selectively drawing samples of blood from two sections of a line comprises a selection element formed with three ways and a seat in which said selection element is housed. There is a first, a second and a third connection, branched out of said seat. The three ways being arranged for selectively connecting two of said three connections between each other upon manual operation of said selection element and said first connection being capable of receiving a line connected to an arterial blood drawing section and the second connection being suitable to be connected to a venous blood drawing section.

There is a first duct and a first trap with an open top part, able to receive a syringe for drawing blood samples. The first trap is connected at a bottom portion through said first duct to said third connection. A first coupling receives a line connected to a drain and is arranged at the bottom portion of said first trap. A first and a second one-way valve with the first one-way valve arranged in said third connection and allowing a flow to occur away therefrom. The second one-way valve is arranged in said first coupling and allows a flow toward said drain. A first sealing surface is between the bottom part and the top of said first trap. A first shutter on said first sealing surface acts in combination therewith. A first spring means between a part of said first trap and said first shutter pushes said shutter against said sealing surface. The first shutter is shaped so as to make contact with a syringe if inserted in said first trap, so as to break contact with said sealing surface when the syringe is inserted into said trap.

Preferably the device further has a second duct and a second trap with an open top part, capable of receiving a syringe for injection of drugs, said second trap being connected at the bottom portion through said second duct to said second connection. A second coupling receives a line connected to a venous blood drawing section at the bottom portion of said second trap. A second sealing surface is between the bottom portion and the top of said second trap and a second shutter on said second sealing surface acts in combination therewith. A second spring means arranged between a part of said second trap and said second shutter pushes said second shutter against said second sealing surface. The second shutter is shaped so as to make contact with a syringe if inserted in said second trap to inject drugs into the blood.

Further features and advantages will become apparent from the description of a preferred but not exclusive embodiment of the invention, illustrated only by way of non-limitative example in the accompanying drawings, wherein:

DETAILED DESCRIPTION OF THE DRAWINGS

Figure 2:
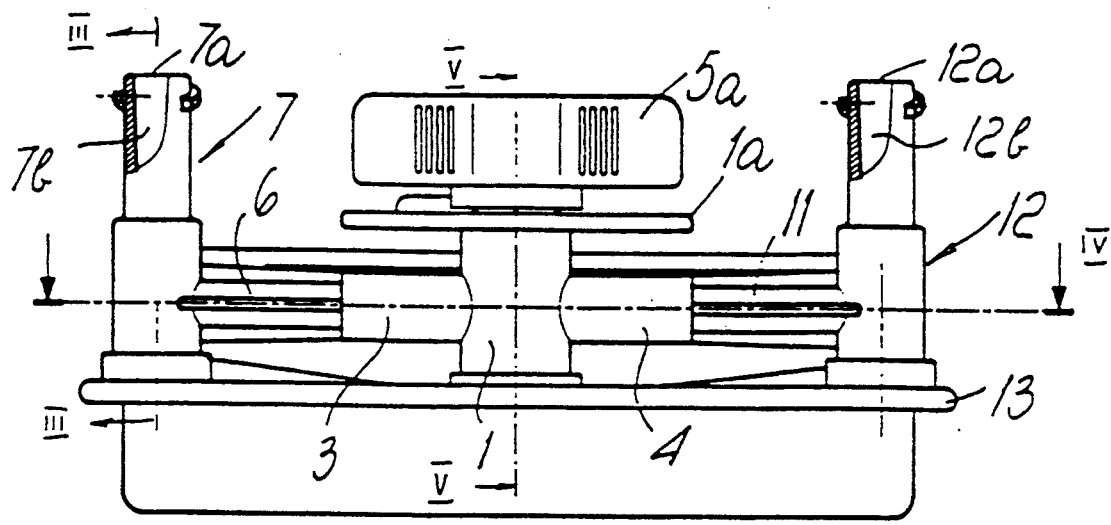
FIG. 2 is a side view thereof.
Figure 1:
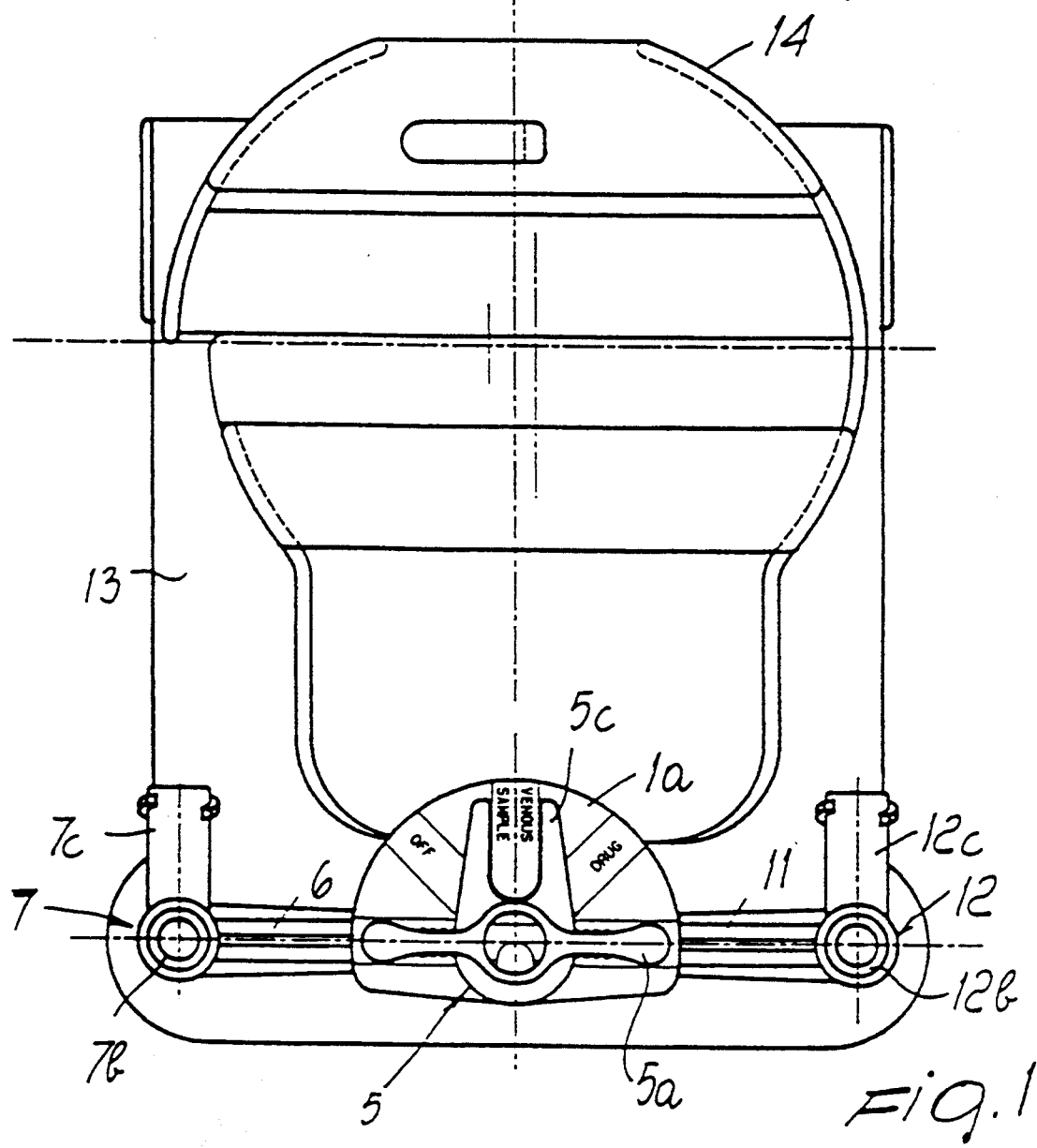
FIG. 1 is a plan view of the device according to the invention.

With reference to the above FIGS. 1 to 5, the reference numeral 1 generally designates the seat provided with the three connections 2, 3, 4 within which the selection element 5 formed with three ways operates. The ways are suitable for selectively connecting any two of said connections upon manual actuation on the part of an operator who grips the wings 5a, as will be described in greater detail in the description of the operation.

Specifically, each of said three connections 2, 3, 4 is angularly spaced relative to one another by 90°, i.e. with respect to the neighboring one in said selection element 5. The three ways of the selection element 5 are in the form of a T-shaped passage designated by 5b.

Figure 3:
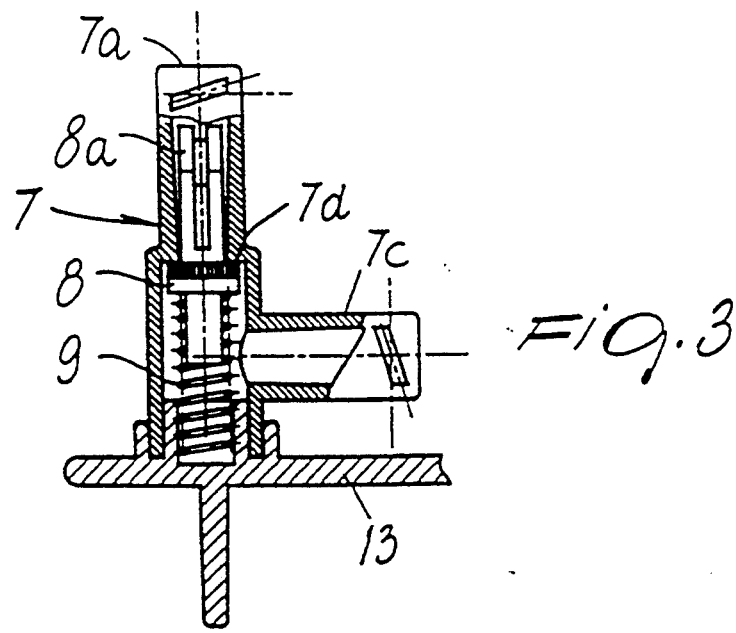
FIG. 3 is a sectional view taken along the plane III—III of FIG. 2.

The connection 2 is intended to receive a line which is connected to an arterial blood drawing section, such as for example the outlet of an oxygenation apparatus (not shown). The connection 3 is connected, by means of the duct 6, to the base of the trap, which is generally designated by the reference numeral 7 and is open at the top 7a. Open top 7a is shaped inside at 7b so as to allow the insertion of a syringe for injecting drugs and extending from the trap 7 near the bottom, there is a coupling 7c, suitable for receiving another line connected to a venous blood drawing section, as for example the inlet of an oxygenation apparatus (not shown). A sealing surface 7d in FIG. 3 is between the bottom and the top of the trap 7 and acts in combination with a shutter 8 pushed against sealing surface 7d by the force of a spring 9. Shutter 8 has a tab 8a which allows it to make contact with a syringe when a syringe (not shown) is inserted in the cavity 7b above the trap 7 so as to break contact with surface 7d.

We shall return to said shutter 8 in describing the operation of the device; for now, it shall be sufficient to note that it constitutes a plug which is suitable to seal and avoid any entry from the outside into the trap 7 and into any line connected to it if no syringe is inserted into cavity 7b.

The connection 4 has the one-way valve 10, which allows the flow of blood only away from the seat 1 and connects by means of a duct 11 to a bottom with a trap 12. The trap 12 is open at a top 12a and is shaped at 12b to allow the insertion of a syringe for drawing samples of blood. A coupling 12c at the bottom is suitable for receiving a further line connected to a drain (not shown). One-way valve 12d allows the flow through coupling 12c of blood only toward said drain.

Like the spring load shutter 8 in FIG. 3, a sealing surface 12e is provided between the top and the bottom of the trap 12 and acts in combination with a shutter 12f which is identical to the shutter 8 and so is not illustrated. Selection element 5 has a fork-like tab 5c in FIG. 1 which is suitable for allowing, between the tines of 5c, the reading of indications provided on an underlying dial 1a rigidly associated with the seat 1 and regarding the various operating positions of the selection element 5. In the condition illustrated in FIG. 1, the indication "venous sample" can be read between the tines of the fork-like tab 5c since the selection element 5 is in the condition which allows to draw venous blood, but by rotating said selection element 5 by 45° clockwise, the indication "drug" becomes visible between the tines, since said selection element 5 is in the condition which allows to inject drugs, and so forth.

The seat 1 and the traps 7 and 12 rest on the plate 13, which has means 14 for containing the lines, not illustrated in the figures, which allow connection of the device to sections for drawing samples of blood and to the drain, when said lines are not in the active condition.

The operation of the device according to the invention is described with reference to FIGS. 6 to 9.

Figure 4:
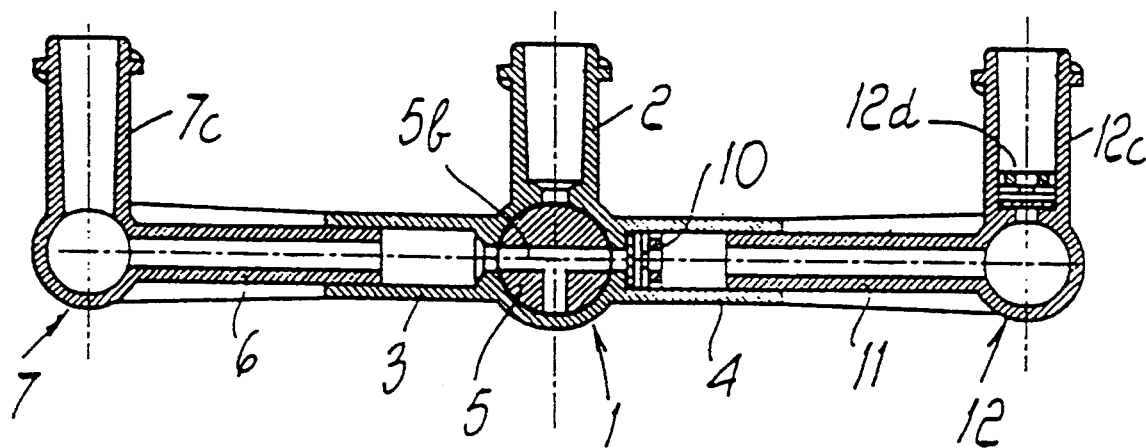
FIG. 4 is a sectional view taken along the plane IV—IV of FIG. 2.
Figure 5:
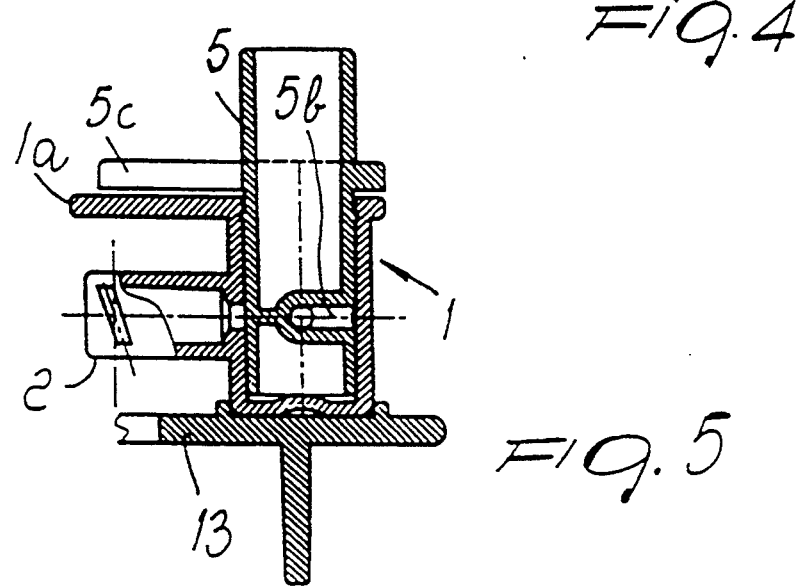
FIG. 5 is a sectional view taken along the plane V-V of FIG. 2.
Figure 6:
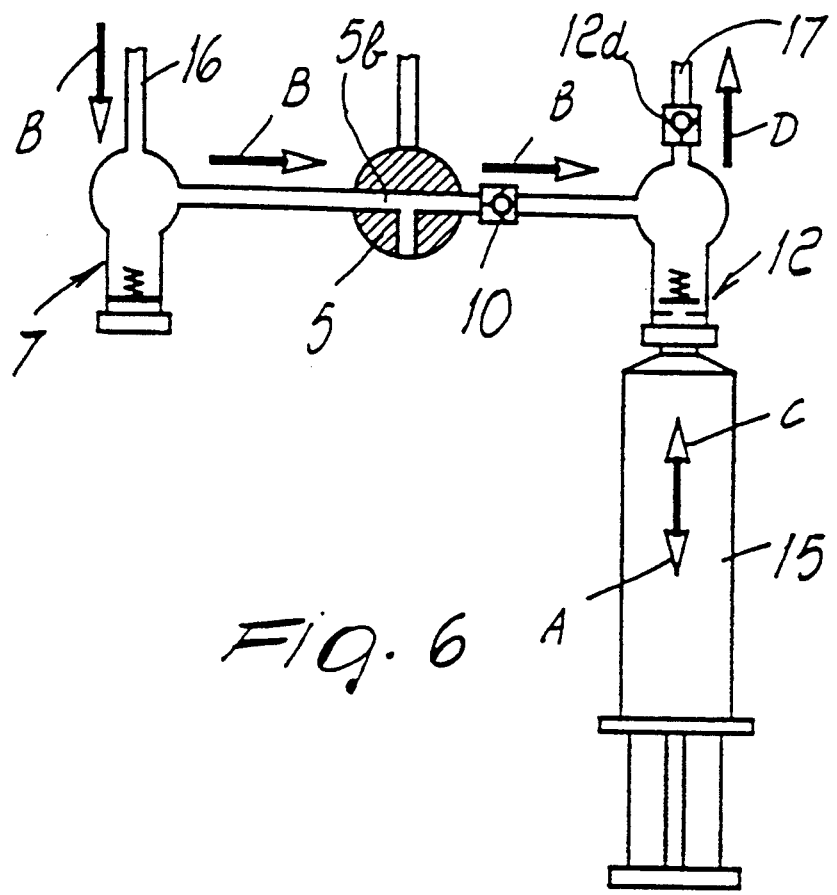
FIGS. 6 to 9 are schematic views of the operating steps of the device according to the invention, which will be illustrated in the description of its operation.

FIG. 6 diagrammatically illustrates the condition of the device when used for the drawing venous blood. A syringe 15 is inserted into the trap 12 and the selection element 5 is arranged so that the passage 5b connects the connections 3 and 4 of the seat 1, as shown in FIG. 4. The insertion of the syringe 15 in the trap 12 causes the separation of the shutter therein from its sealing seat 12e.

The operator starts to draw venous blood by moving the plunger of the syringe 15 in the direction of the arrow A. Venous blood is thus drawn into syringe 15 from line 16 through lines 3 and 4, following the path indicated by the arrows B; in this step, the one-way valve 10 is open and the one-way valve 12d is closed, so that the blood does not reach the drain. It should be noted that the blood cannot escape outside through trap 7, which is closed by the shutter 8.

The blood drawn into the syringe 15 with the described operation is blood which is stagnating in the circuit and is not acceptable for sampling. Thus the operator pushes the plunger of the syringe 15 in the direction of the arrow C, causing the expulsion of the blood along the arrow D through the line 17 which leads to the drain by virtue of the instantaneous closure of the valve 10 and of the simultaneous opening of the valve 12d, see FIG. 6.

The operation is repeated as many times as necessary, until the blood drawn into the syringe 15 is considered a good sample and at this point said syringe is removed from the trap 12. If the selection element 5 has not been moved preliminarily to the "off" position but remains in the drawing position, the blood will not escape from trap 12 because the shutter 12f has resumed its position in contact with the sealing surface 12e.

The presence of said shutter 12f constitutes an operating safety device against the escape of blood from the trap 12 not only in the described step of removal of the syringe 15 at the end of the drawing but also in the step of insertion of syringe 15. That can be performed without problems even if the selection element 5 has been placed in the drawing condition before insertion occurs; also during the steps of actuation of the plunger of the syringe 15, which might cause momentary separation of the syringe 15 from the trap 12.

Figure 7:
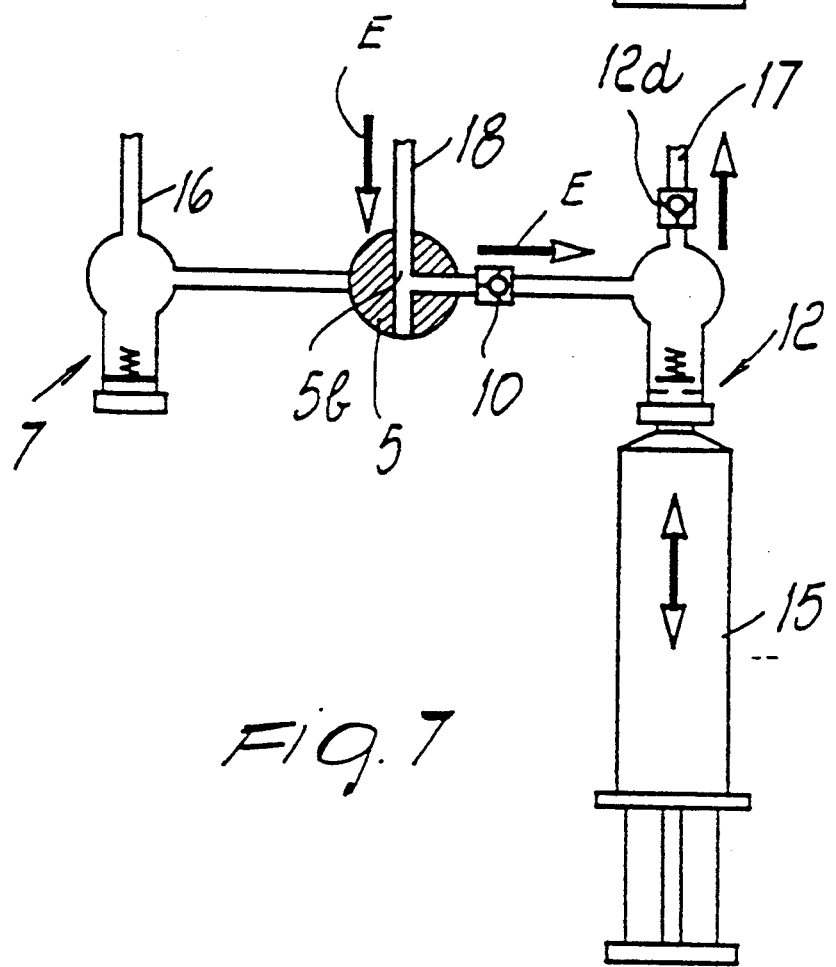

FIG. 7 illustrates the condition for drawing arterial blood, and all that has been said regarding the drawing of venous blood is also true here, except for the different position of the selection element 5, which is now arranged so that the passage 5b connects the connections 2 and 4 through seat 1. That allows arterial blood from the line 18 to move in the directions of arrows E.

Figure 8:
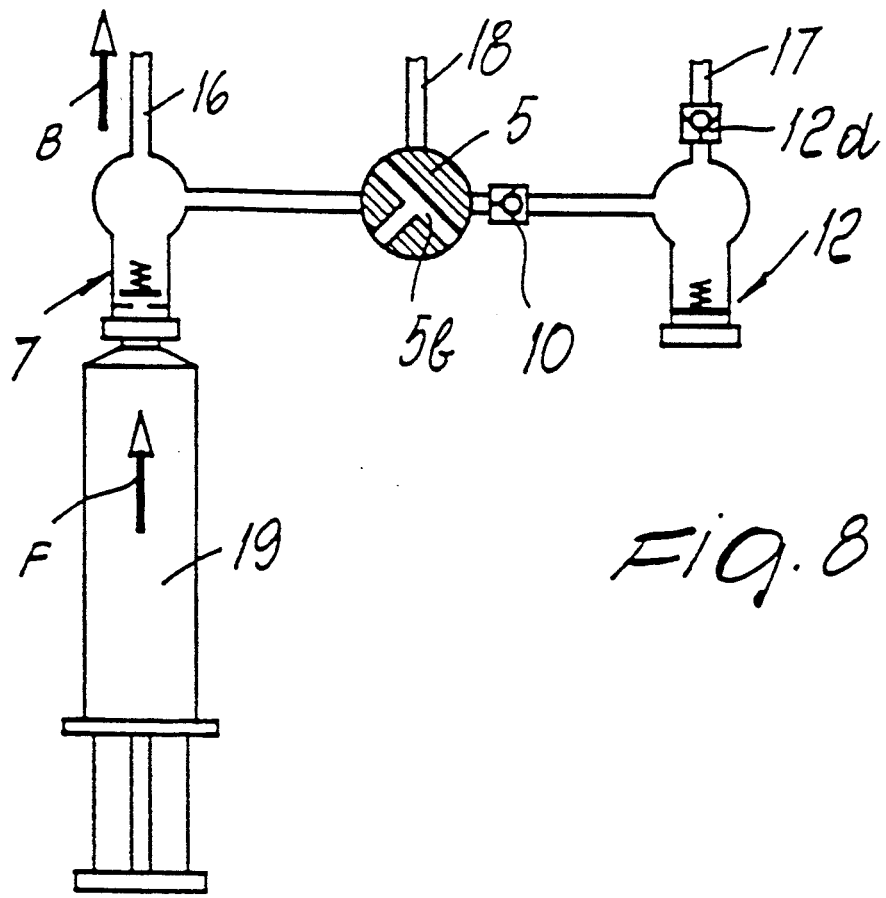

FIG. 8 diagrammatically illustrates the condition for the injection of drugs into the blood. A syringe 19 filled with drug is inserted in the trap 7. The shutter 8 leaves its sealing surface 7d and the selection element 5 is arranged so that the passage 5b does not correspond to any connections to the seat 1. This is the position of the selection element 5 indicated by the marking "drug" on the dial 1a.

In order to inject the drug, the operator moves the plunger of the syringe 19 in the direction of the arrow F, causing the introduction of the drug into the line 16 according to the arrow G.

Figure 9:
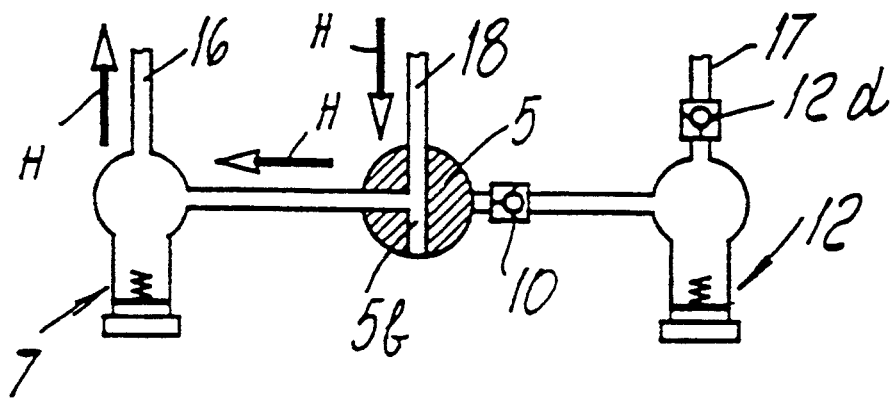

This step must be followed by a step, known as "shunting", in which arterial blood enters the line 16 to cause the complete removal of the drug from that line and this step is the one which occurs with the arrangement of selection element 5 and passage 5b shown in FIG. 9. The syringe 19 has been removed without using any particular precaution, since the shutter 8 will instantly close the trap 7 avoiding escape of blood. The required circulation of blood according to the arrows H from the arterial line 18 to the venous line 16 is created.

The construction and functional simplicity of the device according to the invention is evident. With regard to its functional simplicity, it is sufficient to observe that the presetting of the device for performing each of the possible actions requires the operator to perform a single action on selection element 5. This situation is safe since operating speed error avoidance is easy.

Another positive feature of the invention is prevention of escape of blood from the device, regardless of any situation which occurs as a result of any action by the operator.

The described invention is susceptible to numerous modifications and variations, all of which are within the scope of the inventive concept. All of the specific parts shown may be replaced with other technically equivalent ones.

In the practical execution of the invention, the materials employed, as well as the shapes and dimensions, may be any according to specific requirements.

What is claimed is:

1. A device for selectively drawing samples of arterial and venous blood and for injecting drugs into the blood, comprising:
   (a) a seat having a first, second, and third connection port;
   (b) the first connection port in fluid communication with an arterial blood source for receiving arterial blood;
   (c) the second connection port in fluid communication with a first trap;
   (d) the first trap in fluid communication with a venous blood source, the first trap including means for selectively injecting drugs into the first trap;
   (e) first means for one-way fluid flow interposed between the third connection port and a second trap, wherein blood may flow only in the direction of the second trap;
   (f) second means for one-way fluid flow interposed between the second trap and a drain, wherein blood may flow only in the direction of the drain, the second trap including means for selectively drawing blood samples from the second trap; and
   (g) selection control means operably connected to the seat for selectively directing the flow of blood between any two of the first, second, and third connection ports, wherein the selection control means has (i) a first position where arterial blood flows from the first connection port, through the second connection port, through the first trap, and to the venous blood source, (ii) a second position where venous blood from the venous blood source flows through the first trap, through the second connection port, through the third connection port, to the second trap, and (iii) a third position where arterial blood flows through the first connection port, through the third connection port, to the second trap.

2. The device of claim 1 wherein each of the first, second, and third connection ports are spaced 90° from any adjacent connection port.

3. The device of claim 1 wherein the selection control means includes a T-shaped passageway.

4. The device of claim 1 wherein the first trap includes a first open top portion defining a first cavity for receiving a syringe, a first bottom portion in fluid communication with the venous blood source and the second connection port, first spring-biased sealing means disposed between the first bottom portion and the first top portion for creating a liquid-tight seal between the first bottom portion and the first top portion, a first tab disposed within the first cavity, wherein pressure on the first tab moves first spring-biased sealing mans away from the first top portion, breaking the liquid-tight seal, and allowing fluid communication between the first open top portion and the first bottom portion, and further wherein removing pressure on the first tab allows first spring-biased sealing means to move toward the first top portion to reestablish a liquid-tight seal between the first bottom portion and first top portion.

5. The device of claim 1 wherein the second trap includes a second open top portion defining a second cavity for receiving a syringe, a second bottom portion in one-way fluid communication with the drain and the third connection port, second spring-biased sealing means disposed between the second bottom portion and second top portion for creating a liquid-tight seal between the second bottom portion and the second top portion, a second tab disposed within the second cavity, wherein pressure on the second tab moves second spring-biased sealing means away from the second top portion breaking the liquid-tight seal and allowing any blood in the second bottom portion to flow into the second open top portion, and further wherein removing pressure on the second tab allows second spring-biased sealing means to move toward the second top portion to reestablish a liquid-tight seal between the second bottom portion and second top portion.

6. The device of claim 1 including a dial rotatably associated with the seat, the dial having indicators that represent the positions of the selection control means, and wherein the selection control means includes wings for changing the position of the selection control means and further includes a fork-like tab having two tines so that the position of the selection control means is identified by the dial indicator between the two tines.

7. The apparatus of claim 1 further including a plate connected to the seat and first and second traps for support.

* * * * *